United States Patent
Hall et al.

(10) Patent No.: US 8,323,221 B2
(45) Date of Patent: Dec. 4, 2012

(54) TISSUE TEMPERATURE INDICATING ELEMENT FOR ULTRASOUND THERAPY

(75) Inventors: Christopher S. Hall, Hopewell Junction, NY (US); Ralph Kurt, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 238 days.

(21) Appl. No.: 12/742,016

(22) PCT Filed: Nov. 11, 2008

(86) PCT No.: PCT/IB2008/054718
§ 371 (c)(1),
(2), (4) Date: May 7, 2010

(87) PCT Pub. No.: WO2009/063399
PCT Pub. Date: May 22, 2009

(65) Prior Publication Data
US 2011/0098609 A1 Apr. 28, 2011

Related U.S. Application Data

(60) Provisional application No. 60/987,121, filed on Nov. 12, 2007.

(51) Int. Cl.
*A61H 1/00* (2006.01)
(52) U.S. Cl. .......................................................... 601/2
(58) Field of Classification Search .................. 601/3
See application file for complete search history.

(56) References Cited

U.S. PATENT DOCUMENTS

| 4,459,854 | A | * | 7/1984 | Richardson et al. ............ 73/644 |
| 4,952,033 | A |   | 8/1990 | Davis |
| 5,057,560 | A |   | 10/1991 | Mueller |
| 5,686,153 | A |   | 11/1997 | Heynderickx |
| 5,722,411 | A |   | 3/1998 | Suzuki |
| 5,805,245 | A |   | 9/1998 | Davis |
| 6,165,389 | A | * | 12/2000 | Asher et al. .................... 252/582 |
| 6,454,730 | B1 | * | 9/2002 | Hechel et al. ..................... 601/2 |
| 6,500,133 | B2 |   | 12/2002 | Martin |
| 2005/0236932 | A1 | * | 10/2005 | Nagahara et al. .............. 310/328 |
| 2008/0292167 | A1 | * | 11/2008 | Todd et al. ...................... 382/131 |

FOREIGN PATENT DOCUMENTS

| GB | 2199981 | A1 | 7/1988 |
| WO | 2004003498 | A2 | 1/2004 |
| WO | 2004071278 | A2 | 8/2004 |
| WO | 2005112807 | A2 | 12/2005 |

OTHER PUBLICATIONS

Anonymous: "Thermal Conductivity of some Common Materials—Aluminum, Asphalt, Brass, Copper, Steel and many more.." The Engineering Toolbox, 2005, pp. 1-6.
Anonymous: "Acoustic Properties of Liquids" ONDA Corporation, Apr. 2003.

* cited by examiner

*Primary Examiner* — Tse Chen
*Assistant Examiner* — Hien Nguyen

(57) ABSTRACT

The present invention relates to a hydrogel-containing temperature indicating element for use in ultrasound therapy. The temperature indicating element of the present invention and the therapeutic device and method making use of the same enable in some embodiments an automated adaptation of the power output as a function of the tissue temperature, avoiding therefore overheating or burning of the skin.

20 Claims, 7 Drawing Sheets

TISSUE TEMPERATURE INDICATING ELEMENT FOR ULTRASOUND THERAPY

The present invention relates to a tissue (e.g. skin or mucosa) temperature indicating element for use in ultrasound therapeutic and diagnostic methods and more particularly in high intensity focused ultrasound methods applicable in the treatment of uterine fibroids, malignant masses in the breast, liver, kidneys, and the brain. The present invention also relates to a device and a method for controlling the power output of an ultrasound transducer or the lateral distribution of the emitted power. The present invention also relates to the use of ultrasound transparent and temperature responsive hydrogels for monitoring the tissue (e.g. skin or mucosa) temperature of a mammal exposed to ultrasound energy. The present invention may be used as a dose measurement for ultrasound treatments for wound healing and sports medicine.

High intensity focused ultrasound (HIFU) is currently clinically approved for the treatment of uterine fibroids. Initial results for this technology show that it is a good candidate to remotely destroy undesired tissue deep within the body with minimal side effects to the surrounding structures. This method consists in rapidly heating up pathogenic tissues inside the body in order to allow for coagulative necrosis of those tissues. This is accomplished in HIFU through the use of large aperture transducers which allows for the distribution of acoustic energy to be placed over a larger surface area in the proximal structures (skin, fat, muscle, etc.). A typical ultrasound treatment attempts to raise the tissue to 85° C. in about 15 seconds. For a typical ultrasound beam size of 1.2 mm (in width) by 11 mm (in length), this requires roughly 1250 W/cm2. If the transducer is a 12 cm (F#=1) natural focused transducer (as is the case in the current clinical HIFU systems) placed about 4 cm from the skin surface, the intensity at the skin is 0.25 W/cm2. The amount of energy absorbed at the skin changes drastically as the probe geometry grows smaller and the region of interest becomes more superficial.

One of the remaining challenges for this technology is the need for fast and efficient ways to prevent overheating the patient's tissue (e.g. skin or mucosa). The need to place a considerable amount of energy into the patient's body, in order to heat and maintain a high temperature at the place of interest, has the side effect to heat up the skin of the patient due to the acoustic impedance mismatch between the skin and the coupling medium (usually degassed, actively cooled water). Since this mismatch is often substantial, the patient can suffer important heating of the skin surface which can sometimes lead to discomfort and/or burns. Often, this negative side-effect is made worse by gas bubbles entrapped within the tissue, e.g. at the interface between skin and a coupling agent (e.g. a hydrogel), or on small hairs on the skin.

Several approaches currently exist to monitor the skin temperature including thermocouple monitoring and visual inspection of the skin redness. The thermocouple approach is imperfect in the case of HIFU since the thermocouple leads are not acoustically transparent and can interfere with the acoustic path. This makes adequate spatial sampling difficult and laborious. Monitoring skin color changes can often be difficult as the baseline pigmentation varies from patients to patients, and skin color may not change until the patient has suffered some damage. Moreover observing the redness of the skin tissue does not allow a fast feedback control as redness is a relatively slow reaction of the skin tissue and indicates skin burn, which should be prevented.

U.S. Pat. No. 6,454,730 discloses the application of ultrasonic energy to a portion of a living human body, wherein said use is accompanied by the use of a thin thermally active film deposited on the outer surface of the body portion and which may be used to detect a localized temperature of this portion. The thermally active film change color or opacity at a predetermined temperature. It is thin in order to allow the transducer to be swept over the indicator without interaction with the ultrasonic signal or interference with transmission of the ultrasonic signal into the portion. Such a thin indicator would make any automation of the color detection difficult since a certain thickness is necessary to allow lateral optical detection. Automated vertical detection is hardly an option since the ultrasound transducer is above the indicator and therefore in the way of an eventual light detector. The indicator is used to see when a certain dose is reached and therefore the treatment is completed. It is not intended to prevent skin burn. This is also clear from the target temperature ranges, slightly above body temperature (39° C.). The embodiment of U.S. Pat. No. 6,454,730 suffers from the disadvantage of not enabling a fast enough control of the temperature at the skin surface. Additionally, visual inspection of the thermally active film is unpractical since the ultrasound transducer is in the way of the observer's eye.

There is therefore a need in the art for fast and efficient ways to monitor the skin temperature in order to discontinue or halt the treatment in case of skin over-heating.

An object of the present invention is to avoid over-heating of the tissue (e.g. skin or mucosa) of a mammal experiencing ultra-sound therapy in a fast, safe and reliable way. The above objective is accomplished by temperature indicating elements, methods and devices according to the present invention. Embodiments of the present invention also relate to a therapeutic or diagnostic method using the same. An advantage of many embodiments of the present invention is that the tissue (e.g. skin or mucosa) temperature can be efficiently and cost-effectively monitored and/or controlled by temperature indicating elements transparent to ultrasound waves. Another advantage of many embodiments of the present invention is that the tissue temperature can be monitored easily despite the presence of the ultrasound transducer in the visual field of the operator or despite the fact that the tissue of interest may be an internal mucosa. Yet another advantage of many embodiments of the present invention is that over-heating of the tissue (skin or mucosa) can be automatically prevented without requiring an external intervention of an operator during ultrasound exposure.

Particular and preferred aspects of the invention are set out in the accompanying independent and dependent claims. Features from the dependent claims may be combined with features of the independent claims and with features of other dependent claims as appropriate and not merely as explicitly set out in the claims.

In a first aspect, the present invention relates to a temperature indicating element for topical application, comprising a layer with a thickness ranging from 100 μm to 5 mm of a hydrogel being a temperature indicating agent and/or comprising one or more temperature indicating agents operating by changing an optical property, said hydrogel being substantially transparent to ultrasound energy.

As an advantageous feature of this first aspect of the present invention, the temperature indicating element may operate by changing an optical property at a temperature ranging from about 30° C. to about 70° C. This is advantageous because such temperatures causes at least discomfort or even burns to the relevant tissues (e.g. skin or mucosa) of patients.

As another advantageous feature of this first aspect of the present invention, the hydrogel may comprise a polymer or copolymer having N-substituted acrylamide monomeric moeities. This is advantageous because N-substituted acrylamides polymers and co-polymers have a LCST above which their optical properties change. within such an embodiment, there is no need for an additional temperature indicating agent.

As another advantageous feature of this first aspect of the present invention, the hydrogel may have an acoustic impedance above or equal to 1.4 Mrayl and below or equal to 1.6 Mrayl. This is advantageous because acoustic impedance within these values permits to avoid to a large extent impedance mismatch between the temperature indicating element and the tissue and/or a coupling medium used between a transducer and the relevant tissue (e.g. skin). 1 Mrayl is equal to 1 Pa·s/m.

As an advantageous feature of this first aspect of the present invention, the hydrogel may have a density equal to or above 0.9 g/cm$^3$ and/or equal to or below 1.1 g/cm$^3$ when saturated with water.

As an advantageous feature of this first aspect of the present invention, the sound velocity within the hydrogel may be equal to or above 1.3 mm/µs and/or equal to or below 1.75 mm/µs.

As an advantageous feature of this first aspect of the present invention, the temperature indicating element may have a thermal conductivity k above or equal to 0.15 W/(m*K) and/or below or equal to 0.6 W/(m*K). This embodiment is advantageous because it provides a good thermal contact between the temperature indicating element and the tissue. This makes sure that the temperature indicating element effectively and rapidly measure the temperature of the relevant tissue.

As an advantageous feature of this first aspect of the present invention, the temperature indicating element may be a laminated structure comprising two or more layers of hydrogels. This is advantageous because it permits for instance to integrate several types of temperature indicating hydrogels, each changing an optical property at a different temperature, within the same temperature indicating element. This embodiment also permits to include for instance at least two layers with different acoustic impedances. This is advantageous because it permits to create a gradient of acoustic impedance throughout the thickness of the temperature indicating element, thereby e.g. matching the acoustic impedance of the relevant tissue (e.g. skin) on the one hand and the acoustic impedance of a coupling medium on the other hand. In another embodiment of the present invention, it may also be advantageous to include at least one layer being free of any temperature indicating agent. In particular, this may be the layer in contact with the relevant tissue. This permits to avoid irritation or allergy problems in certain patients. Preferably this outer layer is chosen to be biocompatible and/or hypoallergenic and non-toxic.

In another aspect, the present invention relates to a device comprising:

(a) means for emitting ultrasound energy into a mammalian body having a temperature indicating element placed onto a tissue of said mammalian body, (b) means for detecting a change in optical property of said temperature indicating element, and (c) an alarm for signaling that the change in optical property detected by means (b) is indicative of a temperature value above a predetermined value, and/or a controller for reducing the power output of said means (a) for emitting ultrasound energy when the change in optical property detected by means (b) is indicative of a temperature value above a predetermined value.

This type of device is advantageous because it permits a fast response and an efficient burn prevention during ultrasound energy treatment.

As an advantageous feature of this second aspect of the present invention, said controller (c) may switch off at least partially means (a) when the detected temperature is above 30° C. This embodiment is advantageous because this temperature may cause at least discomfort to certain tissues of patients.

As an advantageous feature, said means (a) are means for emitting high intensity focused ultrasound energy. The use of HIFU is prone to cause heat related skin damages.

In another aspect, the present invention relates to a method to gain temperature related information about the a tissue of a mammalian body exposed to ultrasound energy, said method comprising step of placing a temperature indicating element according to the first aspect of this invention onto said tissue of said mammalian body.

As an additional feature, the method may further comprise a step of detecting a change in an optical property of said temperature indicating element.

In yet another aspect, the present invention relates to a method for controlling the power output of a ultrasound transducer, said method comprising the steps of:

placing a temperature indicating element according to any of claims 1 to 3 onto a tissue of a mammalian body, exposing said mammalian body to the ultrasound field of an ultrasound transducer, detecting a change in optical property of said temperature indicating element, and transferring information related to said change in optical property to a controller for modulating said power output as a function of said change in optical property.

In yet another aspect, the present invention relates to a therapeutic or diagnostic method comprising the step of placing a temperature indicating element as previously defined onto a tissue of a mammalian body.

As an additional feature, the therapeutic or diagnostic method may further comprise the step of exposing said mammalian body to ultrasound energy.

In yet a further aspect, the present invention relates to the use of a hydrogel being a temperature indicating agent or comprising one or more temperature indicating agents operating by changing an optical property for monitoring the temperature of a tissue of a mammalian body exposed to ultrasound energy. This is advantageous because such a hydrogel is transparent to ultra-sound waves, therefore preventing absorption and/or scattering of said waves. The hydrogel therefore does not itself acts as a source of heat and it does not interact with the ultrasonic signal or interference with transmission of the ultrasonic signal. When used directly on the skin, it is also highly biocompatible, therefore avoiding skin irritation.

As an optional feature, the hydrogel may comprise a polymer or copolymer having N-substituted acrylamide monomeric moieties. The teachings of the present invention permit the design of improved methods and apparatus for avoiding over-heating of the tissue (skin or mucosa) of a mammal experiencing ultra-sound diagnostic or therapy.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

In the different figures, the same reference signs refer to the same or analogous elements.

Figure 6:
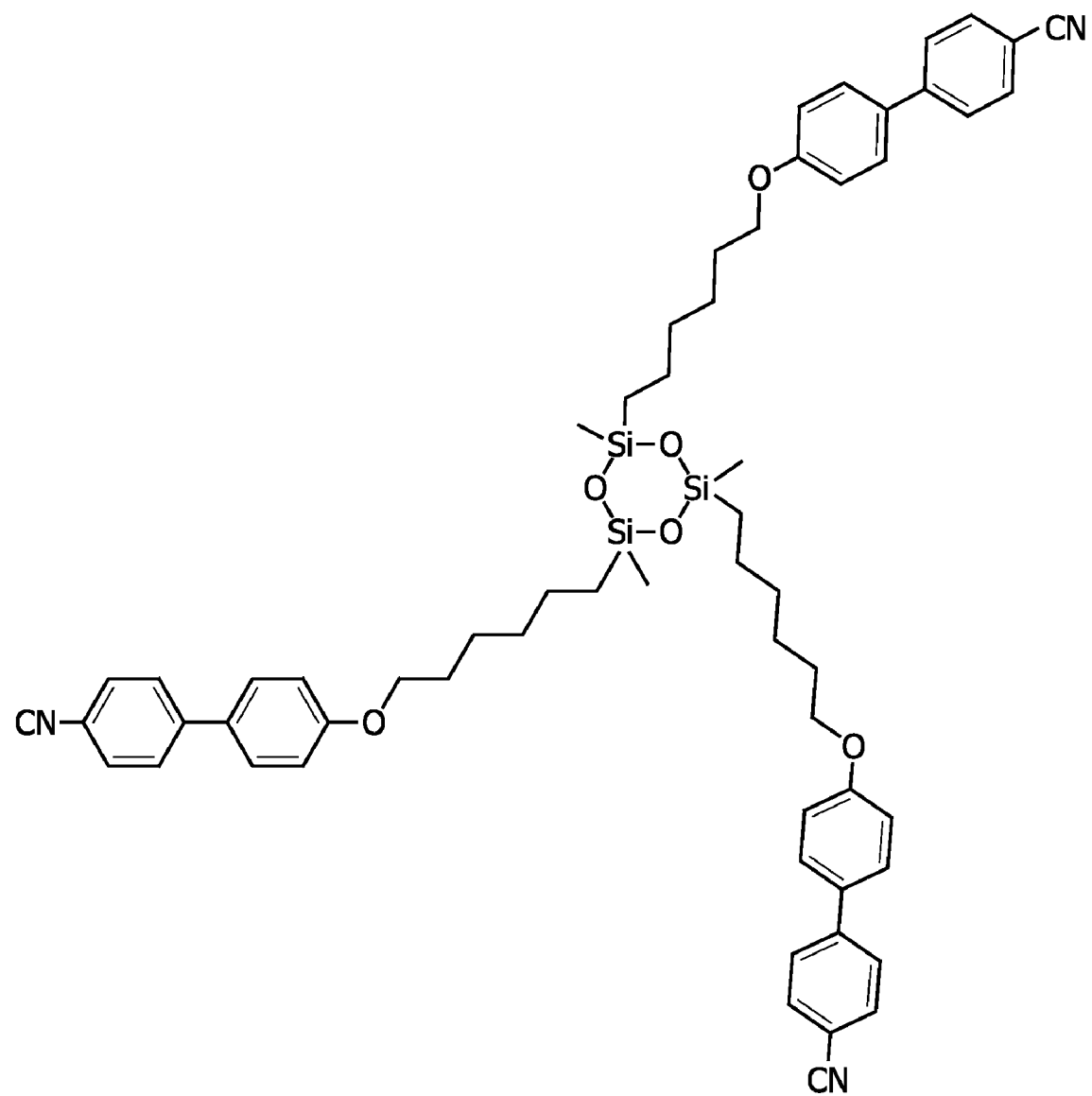

FIG. 6 is the chemical structure of a particular example of a siloxane ring liquid crystal usable as a temperature indicating agent according to an embodiment of the present invention.

Figure 7:
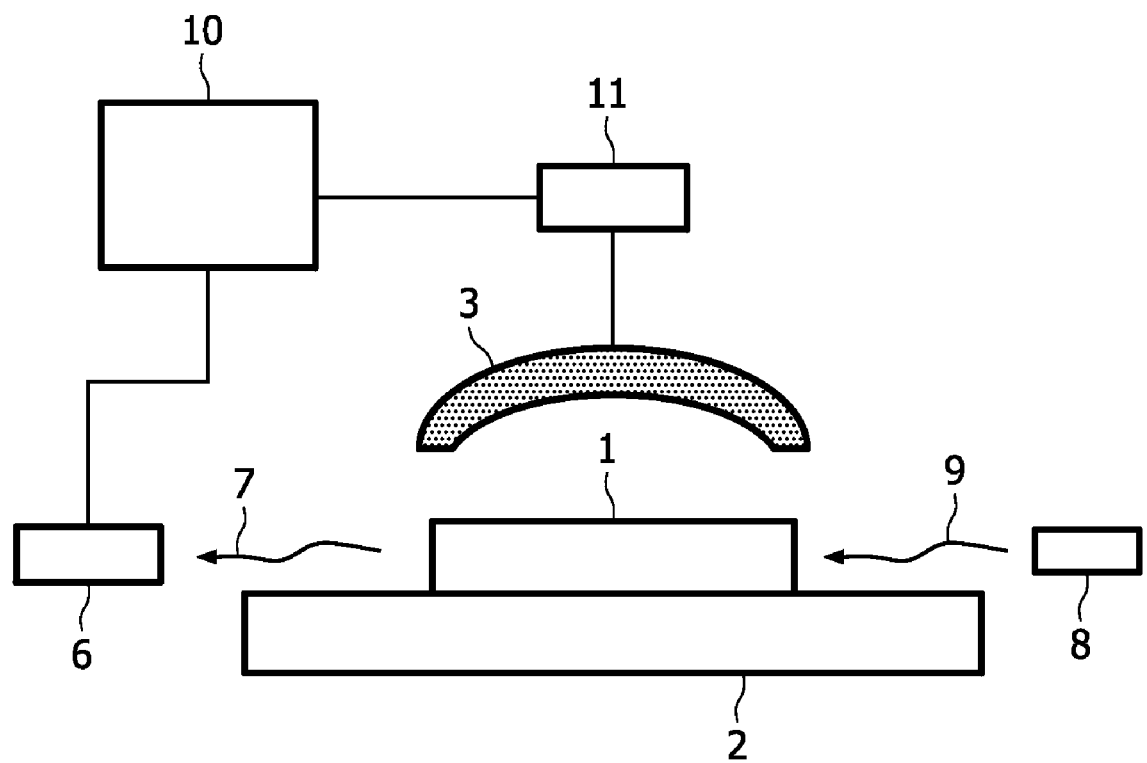

FIG. 7 is a schematic representation of a device according to a particular embodiment of the present invention.

The present invention will be described with respect to certain particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes.

Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

The following term and definition is provided solely to aid in the understanding of the invention.

As used herein, and unless stated otherwise, the term "hydrogel" designates a polymer network capable of swelling in water and other aqueous media, and retaining large volumes of water in the swollen state. In the swollen state, hydrogels consist of a three-dimensional network of polymer chains that are solvated by water molecules while the chains are chemically or physically linked to each other, thus preventing the polymer network from dissolving in the aqueous environment.

As used herein, and unless provided otherwise, the term "tissue" relates to an aggregate of cells usually of a particular kind together with their intercellular substance that form one of the structural materials of an animal such as a mammal or more in particular, a human. Examples of tissues (e.g. from which the temperature can be measured) comprise but are not limited to skin and mucosis (e.g. rectal wall, bladder wall, urethral wall, and uterus wall).

In a first aspect, the present invention relates to a temperature indicating element for topical use, e.g. on the surface of a body exposed to energy via energy supplying means. The type of energy used for such exposure is preferably ultrasound energy and most preferably high intensity focused ultrasound energy (hereinafter abbreviated as HIFU). The energy supplying means is preferably an ultrasound source, most preferably a HIFU source. The body exposed to ultrasound energy may be a living mammalian body, e.g. a human body. The temperature indicating element of the present invention is particularly suitable for indicating the temperature of the skin of a mammalian body experiencing an energetic treatment such as for instance, but not limited to, the cauterization or necrosis of undesired tissue, the production of coagulation necrosis lesions in specific complexes of the brain, the treatment of benign prostatic hyperplasia, prostate cancer, testicular cancer, liver cancer, kidney cancer, ovarian cancer, breast adenoma, ocular adenoma, and the treatment of uterine fibroids by HIFU.

In an embodiment, the temperature indicating element of the present invention changes one or more of its optical properties as a function of temperature.

Non-limiting examples of a change of optical property that can indicate a temperature change within the meaning of the present invention include, but are not limited to, a change in color, absorption, transmission, polarization, index of refraction, scattering, measured light intensity, excitation, fluorescence, reflection, optical in- or out-coupling and the like.

Typically, the change of optical property is observed when a given range of temperatures is reached and/or passed, the measurement of this property permits therefore to determine whether the temperature of a tissue (e.g. skin or mucosa) is above or under this temperature range. Preferably, this change in an optical property is detectable when the temperature of tissue (e.g. skin or mucosa) having temperature indicating elements thereon, is more than or equal to 30° C., for instance more than or equal to 35° C., e.g. more than or equal to 40° C., e.g. more than or equal to 45° C., e.g. more than or equal to 48° C. A five minutes exposure to a temperature of 49° C. can already cause first degree burns. Preferably, this change in an optical property is detectable when the temperature of tissue (e.g. skin or mucosa) having temperature indicating elements thereon, is less than or equal to 70° C., e.g. less than or equal to 65° C., e.g. less than or equal to 60° C., e.g. less than or equal to 55° C. Also preferably, this change in optical property preferably occurs, or is readily detectable, within a temperature range of not more than about 3° C., more preferably within a range of not more than 1° C. This feature is advantageous because it permits to accurately assess the temperature of the tissue surface, e.g. the mammalian skin surface.

The temperature indicating element comprises one or more temperature indicating agents operating by changing their optical properties. Preferably, the temperature indicating element is substantially transparent to ultrasound energy. This is advantageous because it prevents to a large extent the temperature indicating element to itself act as an additional source of heat by minimizing absorption and/or scattering of the ultra-sounds waves by the temperature indicating element. Minimizing absorption and/or scattering of the ultrasound waves also avoids to a large extent that ultrasound energy arrives at a location or with an intensity that is not the location or intensity originally planned. Preferably, the thickness of the temperature indicating element according to an embodiment of the present invention is 30 µm or more, 100 µm or more, 150 µm or more, 200 µm or more, or 300 µm or more. Preferably, the thickness of the temperature indicating element according to an embodiment of the present invention is 5 mm or less, 4 mm or less, 2 mm or less, or 1 mm or less. Within certain embodiments of the present invention, providing a temperature indicating agent which is relatively thick may be advantageous because it enables lateral optical detection (i.e. optical detection parallel to the skin), e.g. it permits optical detection despite the presence of an ultrasound transducer placed above the temperature indicating agent. It also facilitates the optical detection within cavities, e.g. when the temperature indicating element is applied onto an internal mucosa. In a preferred embodiment of the present invention, the temperature indicating element is applied and/or maintained during the ultrasound treatment in the ultrasound field, i.e. in the direct path of the ultrasound. This is in contrast with U.S. Pat. No. 6,454,730 wherein the thin thermally active film disclosed is outside the ultrasound field when the dose is measured. The temperature indicating element of the present invention may comprise an encapsulated fluid, a plastic polymer, a gel and/or a solid. In an embodiment, a temperature indicating element of the present invention comprises a hydrogel. In some embodiments of the present invention, an ultrasound transparent material coated or impregnated with a thermochromatic hydrogel may be used. In some other embodiments of the present invention, a temperature sensitive hydrogel may be embedded into a thicker hydrogel layer. In certain embodiments, the temperature indicating element of the present invention may change its optical property within a time period of less than 50 ms. Hydrogels contain a significant amount of water. This reduces to a large extent the impedance mismatch between the tissue (e.g. skin or mucosa) and the temperature indicating element. The amount of energy absorbed at the interface between tissue (e.g. skin or mucosa) and the temperature indicating element is therefore minimized. Also, in ultrasound-based therapeutic and diagnostic methods, a water-based coupling medium may be used between the surface of the body and the ultrasound transducer. Hydrogels being or comprising a temperature indicating agent according to certain embodiments of the present invention are highly compatible with such a coupling medium and impedance mismatch between the coupling medium and the temperature indicating element is therefore minimized. According to a further embodiment of the present invention, the temperature indicating element may replace, totally or partially, the said coupling medium. The present invention therefore also relates in one embodiment to a coupling medium for use between an ultrasound transducer and a mammalian body, said coupling medium comprising a hydrogel being or comprising a temperature indicating agent. According to an embodiment of the present invention, the hydrogel is designed to itself constitute the temperature indicating agent. In another embodiment of the present invention, the hydrogel comprises one or more species being temperature indicating agents, e.g. temperature indicating agents are dispersed, for instance homogeneously dispersed, within the hydrogel mass. It is also possible for the hydrogel to be a temperature indicating agent and additionally include one or more species being temperature indicating agents. In certain embodiments of the present invention, the temperature indicating element may comprise a coloring agent. This is advantageous because it permits to adapt the color of the tissue onto which the temperature indicating element is applied. Preferably, the hydrogel may be adapted to match the acoustic properties of the tissue and/or of the coupling agent (e.g. water or a hydrogel). This is advantageous because it permits to adapt the acoustic properties (e.g. acoustic impedance) of the temperature indicating element to various type of tissues (e.g. various types of skins, e.g. varying in their collagen or elastin content). In an advantageous embodiment of the present invention, the temperature indicating element comprises two or more layers of hydrogels wherein each layer has an acoustic impedance different from the neighboring hydrogel layers. This is advantageous because it permits to achieve an acoustic impedance close to the acoustic impedance of a coupling agent (e.g. water or a hydrogel) at one side of the temperature indicating element and to gradually change the acoustic impedance of the temperature indicating element to reach the acoustic impedance of the relevant tissue (e.g. skin) at the opposite side of the temperature indicating element. Optionally, each layer may comprise a different temperature indicating agent changing its optical properties at a different temperature. In certain embodiments of the present invention, a skin protective layer can be applied as a top or bottom layer of a temperature indicating element. Such a skin protective layer can be for instance a layer of biocompatible material (e.g. a hydrogel) for instance being free of potentially irritating temperature indicating agents. This embodiment can help preventing irritation or allergy problems for instance in certain patients.

Non-limiting examples of temperature indicating agents suitable for use in the present invention are temperature responsive polymers (particularly temperature responsive biocompatible polymers exhibiting sufficient hydrophilic properties for forming hydrogels), thermochromic dyes, photochromic dyes (e.g. dispersible into a biocompatible polymer matrix) and liquid crystals. Due to the intended topical administration or application concerned by the present invention, it is obviously desirable that any temperature indicating agent being selected as a hydrogel, or for inclusion into a hydrogel according to this invention, be biocompatible with the type of tissue (e.g. mucosa or skin) to which it is directly attached, in particular does not cause any form of skin irritation or allergy.

In another embodiment of the present invention, temperature responsive materials undergoing a phase transition (including melting, crystalline-amorphous transition, LCST or other transitions) may be used as temperature indicating agents. For instance, (hydrophilic) polymers, co-polymers or hydrogels exhibiting a lower critical solution temperature (LCST) may be used as temperature indicating agents. These polymers, co-polymers or hydrogels switch from a transparent to a scattering state above the LCST. Non limitative examples of temperature responsive polymers includes polymers, co-polymers or hydrogels based on one or more of the following monomers: N-substituted acrylamides (such as N-alkylacrylamides, as N-isopropylacrylamide, di(m)ethylacrylamide, carboxylsopropylacrylamide, hydroxymethylpropylmethacrylamide, etc), acryloylalkylpiperazine and N-vinylcaprolactam as well as co-polymers thereof with hydrophilic monomers such as but not limited to hydroxyethyl(meth)acrylate, (meth)acrylic acid, acrylamide, polyethyleneglycol(meth)acrylate, N-vinylpyrrolidone, dimethylaminopropylmethacrylamide, dimethylaminoethylacrylate, N-hydroxymethylacrylamide or mixtures thereof, and/or co-polymerized with hydrophobic monomers such as but not limited to (iso)butyl(meth)acrylate, methylmethacrylate, isobornyl(meth)acrylate, glycidyl methacrylate or mixtures thereof. Examples of useful polymers are poly(N-isopropyl acrylamide) (LCST=32° C.), poly(N,N'-diethyl-acrylamide) (LCST=25 to 35° C.) and poly(-N-acryloyl-N'-alkylpiperazine) (LCST=37° C.). The N-substituted acrylamides may be copolymerized with for instance oxyethylene, trimethylolpropane distearate, $\epsilon$-caprolactone and mixtures thereof among others. The skilled person is able to design monomer mixtures, in terms of monomer selection and proportions of monomers, that are able to tailor a desirable LCST at will above body temperature, e.g. within a range from about 30° C. to about 70° C.

Figure 4:
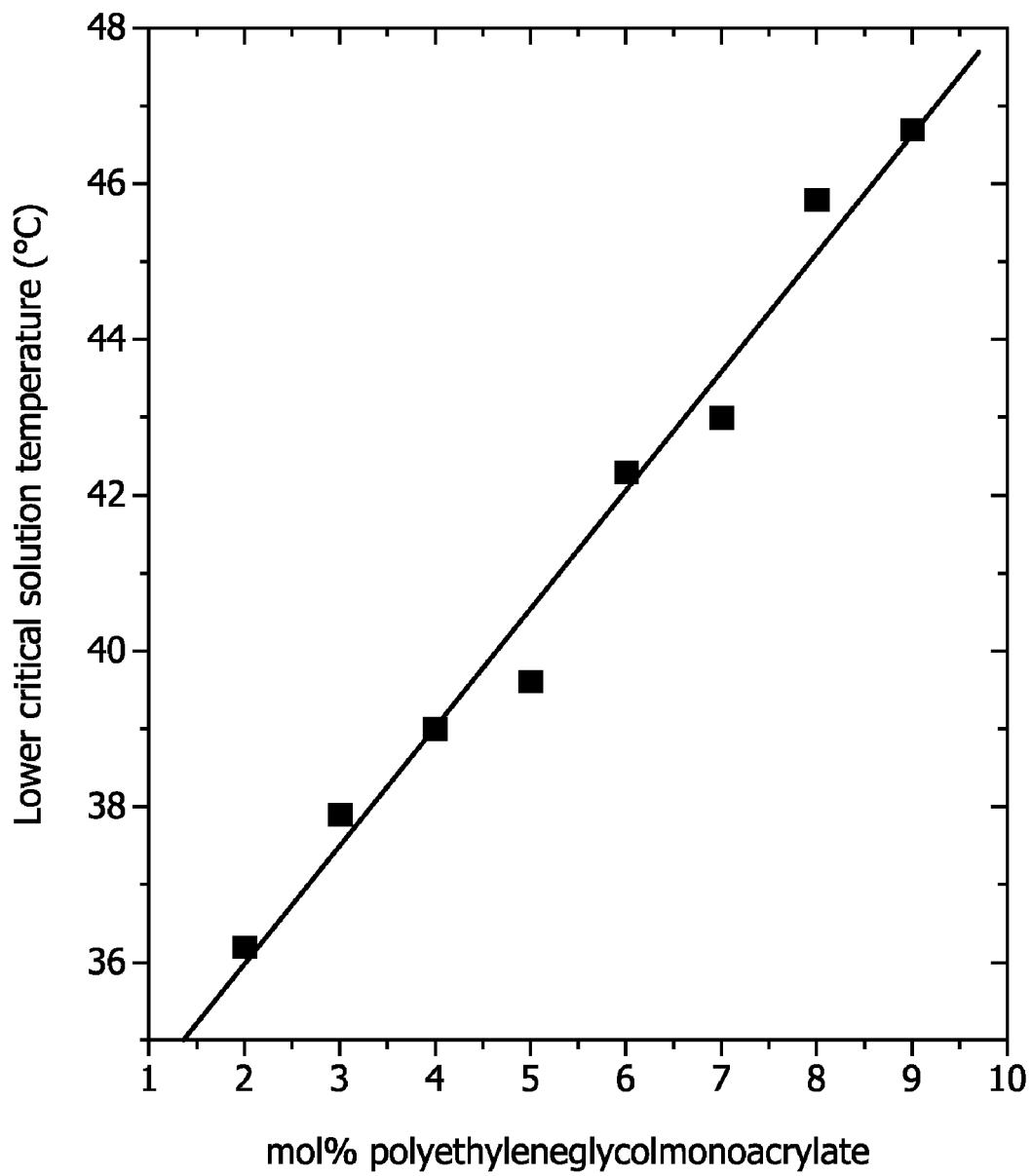
FIG. 4 is a graph of the fluorescence intensity versus temperature for hydrogels used in embodiments of the present invention.

Temperature responsive and biocompatible polymer hydrogels may be made for instance by mixing one or more of the above-listed monomers with an effective amount of one or more known crosslinking agents in the presence of an aqueous medium (e.g. water or a water/methanol mixture), and bringing the resulting mixture to a temperature range where partial or complete polymerisation and crosslinking occurs. As is well known to the skilled person, appropriate selection of the monomers, the crosslinking agent type and amount, and/or the polymerization conditions (temperature and time), is able to tailor the LCST and the viscosity of the resulting polymer hydrogel at will. Suitable but non-limiting examples of monomer mixtures comprise N-isopropyl acrylamide-polyethyleneglycol monoacrylate mixtures wherein the polyethyleneglycol monoacrylate amounts from about 2% by mole to about 20% by mole of the monomer mixture. Other suitable comonomers include, but are not limited to, dimethylaminopropyl methacrylamide, N-hydroxymethylacrylamide, glycidyl methacrylate and the like. FIG. 4 the LCST observed for such copolymers in the range of polyethyleneglycol monoacrylate contents from 2% to 9% by mole. Suitable examples of crosslinking agents for the aqueous phase (co)polymerisation of N-substituted acrylamides include, but are not limited to, N-methyl-bisacrylamide, diethyleneglycol diacrylate. The molar ratio monomer(s):crosslinker may suitably be in the range between 1:25 and 1:1000. Furthermore, an initiator (either a photo-initiator or a thermal initiator) may be added in order to initiate polymerization, e.g. in a 1 to 5 weight % ratio with respect to the monomer(s). The one or more monomers are preferably mixed with an aqueous solvent medium ($H_2O$ or a $H_2O$/methanol mixture) typically in an amount between about 50 and about 90% by weight of the total mixture, and the mixture is subsequently (co)polymerized until a hydrogel is formed.

As another advantageous feature of certain embodiments of the present invention, the temperature indicating element may be a hydrogel substrate, or more generally a material that undergoes a phase transition (this includes melting, crystalline-amorphous, LCST or other transitions), having its phase transition (e.g. LCST (lower critical solution temperature)) within a range from about 30 to 70° C., preferably between 40 and 60° C.

As an optional feature of certain embodiments of the present invention, at least one of the one or more temperature indicating agents may comprise a coloring agent, preferably a fluorescent agent such as e.g. a fluorescent dye or fluorescent beads. This feature is advantageous because it renders the temperature transitions more visible.

As another optional feature of embodiments of the present invention, the temperature indicating element may comprise two or more temperature indicating agents, each changing an optical property in a different range of temperature. This is advantageous because it permits to assess the temperature of the mammalian tissue on which the temperature element is applied over a wider temperature range.

As another optional feature, the one or more temperature indicating element may comprise both, a temperature responsive polymer, co-polymer or hydrogel and a coloring agent. The coloring agent (e.g. fluorescent beads) may for instance be embedded within the temperature responsive polymer, co-polymer or hydrogel or may be co-polymerized with the temperature responsive polymer, co-polymer or hydrogel or may be deposited onto the polymer, co-polymer or hydrogel before the deposition of the temperature responsive polymer, co-polymer or hydrogel. This embodiment is advantageous because this permits the detection of a change of intensity in the optical signal detected (e.g. fluorescence of the fluorescent beads) caused by temperature induced scattering of the temperature responsive polymer, co-polymer or hydrogel.

Preferably the hydrogel materials that may be used in certain embodiments of the present invention comprise, in the swollen state, $\geq 50\%$ by weight water and/or solvent, e.g. $\geq 70\%$ by weight, or e.g. $\geq 90\%$ by weight, whereby preferred solvents include organic solvents, preferably organic polar solvents and most preferred alkanols such as ethanol, methanol and/or (iso-)propanol.

According to an embodiment of the present invention, the hydrogel material may comprise a material selected out of the group comprising poly(meth)acrylic materials, silica gel materials, substituted vinyl materials or mixtures thereof.

According to another embodiment of the present invention, the hydrogel material may comprise a poly(meth)acrylic material obtained from the polymerization of at least one (meth)acrylic monomer and at least one polyfunctional (meth)acrylic monomer.

According to another embodiment of the present invention, the (meth)acrylic monomer is selected from the group consisting of (meth)acrylamide, (meth)acrylic acid, hydroxyethyl(meth)acrylate, ethoxyethoxyethyl(meth)acrylate or mixtures thereof among others.

According to another embodiment of the present invention, the polyfunctional (meth)acrylic monomer is a bis-(meth) acrylic and/or a tri-(meth)acrylic and/or a tetra-(meth)acrylic and/or a penta-(meth)acrylic monomer.

According to another embodiment of the present invention, the polyfunctional (meth)acrylic monomer is selected from the group consisting of bis(meth)acrylamide, tripropyleneglycol di(meth)acrylates, pentaerythritol tri(meth)acrylate, polyethyleneglycol di(meth)acrylate, ethoxylated bisphenol-A-di(meth)acrylate, hexanediol di(meth)acrylate or mixtures thereof in any suitable proportions, among others.

According to an embodiment of the present invention, the hydrogel material may comprise an anionic poly(meth)acrylic material, preferably selected from the group consisting of (meth)acrylic acids, arylsulfonic acids, especially styrenesulfonic acid, itaconic acid, crotonic acid, sulfonamides or mixtures thereof, and/or a cationic poly(meth)acrylic material, preferably selected from the group consisting of vinyl pyridine, vinyl imidazole, aminoethyl (meth)acrylates or mixtures thereof, co-polymerized with at least one monomer selected from the group of neutral monomers, preferably selected from the group consisting of vinyl acetate, hydroxyethyl (meth)acrylate (meth)acrylamide, ethoxyethoxyethyl (meth)acrylate or mixtures thereof in any suitable proportions, among others.

According to another embodiment of the present invention, the hydrogel material may comprise a silica gel material.

According to another embodiment of the present invention, the hydrogel material may comprise a substituted vinyl material, preferably vinylcaprolactam and/or substituted vinylcaprolactam.

According to another embodiment of the present invention, the crosslinking density in the poly(meth)acrylic material may be $\geq 0.0001$ and/or $\leq 0.1$, e.g. $\geq 0.001$ and/or $\leq 0.05$, or e.g. $\geq 0.005$ and/or $\leq 0.01$.

Preferably, the cross-linking density of the hydrogel materials used in embodiments of the present invention is such as to make it sticky to the tissue, particularly when the hydrogel contains water or when saturated with water.

In the sense of the present invention, the term "crosslink density" refers to a value $\delta_X$ being defined as $$\delta_X = \frac{X}{L+X}$$

wherein X is the mole fraction of the polyfunctional monomers and L the mole fraction of the linear chain (i.e. non polyfunctional) forming monomers. In a linear polymer $\delta_X=0$, in a fully crosslinked system $\delta_X=1$.

According to another embodiment of the present invention, the temperature indicating agent of the present invention comprise one or more thermo-responsive hydrogel materials based on monomers selected from the group consisting of N-isopropylamide, diethylacrylamide, carboxylsopropylacrylamide, hydroxymethylpropylmethacrylamide, acryloylalkylpiperazine and copolymers thereof with monomers selected from the group of the hydrophilic monomers, this group comprising hydroxyethyl(meth)acrylate, (meth)acrylic acid, acrylamide, polyethyleneglycol(meth)acrylate or mixtures thereof, and/or co-polymerized with monomers selected from the group of hydrophobic monomers, comprising (iso)butyl(meth)acrylate, methylmethacrylate, isobornyl (meth)acrylate or mixtures thereof in any suitable proportions. These co-polymers are known to be thermo-responsive and therefore may be of use as temperature indicating elements within the present invention.

In addition to thermoresponsive biocompatible polymers, suitable temperature indicating agents also include thermochromic dyes. Thermochromic dyes are chemical compounds showing a change of color (usually from a colorless to a colored form) upon a certain change of chemical or physical environment (typically a change of pH and/or temperature). One or more thermochromic dyes is (are) usually enclosed within microcapsules together with a dissociable salt, a weak acid and/or an appropriate solvent. Other type of mixtures using bases instead of acids are also known in the art. When the solvent is solid, i.e. below its melting temperature, the dye exists in its uncolored form, while when the solvent melts, the salt dissociates, the pH inside the microcapsule lowers, the dye becomes protonated, its chemical structure changes, and its absorption spectrum therefore shifts. A number of suitable thermochromic dyes are known in the art and comprise, but are not limited to, spirolactones, fluorans, spiropyrans, and fulgides. A representative example of a thermochromic spirolactone is crystal violet lactone depicted below in both forms.

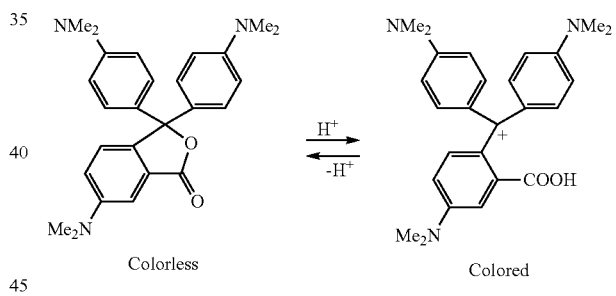

Colorless                    Colored

Suitable weak acids for formulating thermochromic dyes include bisphenol A, parabens, 1,2,3-triazole derivatives and 4-hydroxycoumarin, which act as proton donors, thus changing the dye molecule from its uncolored form to its protonated colored form. These thermochromic dyes can be used in combination with other pigments or dyes producing a color change between the color of the base pigment or dye and the color of the protonated form of the thermochromic dye. Thermochromic dyes are available over a whole temperature range between about −5° C. to 60° C., and in a wide range of colors. The color change of thermochromic dyes usually happens within a 3° C. interval. According to an embodiment of the present invention, the thermochromic dye may be blended with one or more hydrogel-forming monomers or dissolved therein. The solution or blend is subsequently polymerized. This permits to disperse efficiently the thermochromic dye in the hydrogel and to avoid to a large extent contact between the thermochromic dye and the skin.

Another class of temperature indicating agents are photochromic dyes, for which the rate constants of the photochromic processes are strongly dependent upon the amount of free volume in the polymer hydrogel in which they are embedded, and therefore strongly dependent on temperature. For most sterically hindered photochromic compounds the free volume in a polymer hydrogel matrix below the glass transition temperature ($T_g$) may be insufficient for isomerization reactions of the photochromic dye. Above the $T_g$ of the polymer there is a significant increase in the rate constants of the photochromic processes as a result of the increased free volume, and optical changes may then occur. According to an embodiment of the present invention, the photochromic dyes may be blended with one or more hydrogel-forming monomers or dissolved therein. The solution or blend is subsequently polymerized. This permits to disperse efficiently the photochromic dyes in the resulting hydrogel and to avoid to a large extent contact between the photochromic material and the skin.

Other suitable temperature indicating agents are thermotropic liquid crystalline materials. Liquid crystals are available and obtainable within a wide range of liquid to liquid-crystal transition temperatures, especially from about 40° C. to about 70° C. A particularly suitable example of a liquid crystalline material is a polymeric liquid crystalline material such as siloxane polymer backbone having as side side-chains liquid crystals. Other particularly suitable examples of liquid crystalline materials are liquid crystalline siloxane rings. Such (typically high molecular weight) liquid crystalline materials advantageously have a low tendency to diffuse out of a polymer hydrogel, a low water uptake tendency and a relatively sharp liquid-to-liquid crystal transition.

In the case of liquid crystalline temperature indicating agents, this change will usually occur within a sharper interval of temperatures when the purity of the liquid crystal materials is higher. Such an increase of purity usually goes together with an increase of cost. A balance must therefore be found between cost and desired precision of the temperature indication. In most cases, liquid crystals change from a liquid crystalline light scattering state to an isotropic transparent state above a distinctive transition temperature. This change can be used to indicate a temperature as for instance shown in U.S. Pat. No. 5,686,153. When heated up above a certain temperature, liquid crystals can provide an observable transition between a more or less transparent state (depending on the matching of the refractive indexes between the biocompatible hydrogel and the isotropic phase of the liquid crystal used) and a scattering state. An advantage of using low molecular weight liquid crystals is that the temperature range over which the phase transition occurs is relatively small. The adaptation of this temperature range is done for instance by blending different liquid crystals. A potential drawback of low molecular weight liquid crystals may be the diffusion of these liquid crystals out of the hydrogel and a certain degree of water uptake by these liquid crystals. Other temperature indicating agents suitable for the present invention are polymeric liquid crystals (PLCs) which have the advantage of a lesser tendency to diffuse out of the hydrogel and to absorb water. A potential drawback of most polymeric liquid crystals may be that the temperature range over which the phase transition occurs is larger than for low molecular weight liquid crystals. The temperature related information retrieved from these polymeric liquid crystals is nevertheless precise enough for efficiently monitoring tissue (e.g. skin or mucosa) temperature. Among the classes of polymeric liquid crystals, a particular example comprises side-chain liquid crystals with a siloxane polymer backbone.

Figure 5:
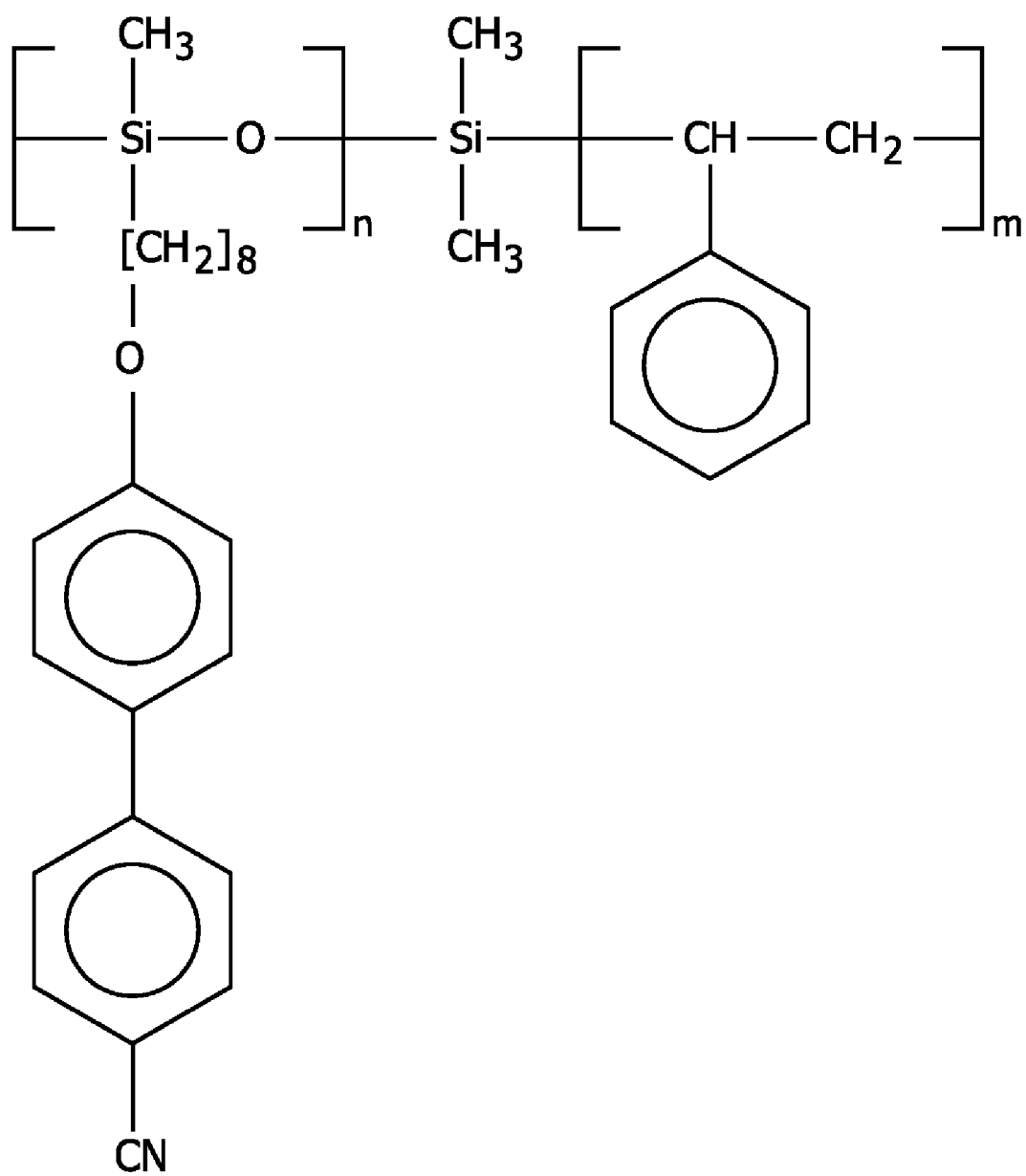
FIG. 5 is a graph of the lower critical solution temperature versus the monomer composition for 8 hydrogels used in embodiments of the present invention.

The polymeric liquid crystal of FIG. 5 is a siloxane-polystyrene block-copolymer, containing cyanobiphenyls side groups at the siloxane chains for providing a liquid crystalline phase. This polymer is in a smectic phase (i.e. a phase in which long range orientation order exist and where the liquid crystalline moieties are grouped into layers) below about 70° C. and has a relatively sharp transition within 5° C. around 70° C. showing a change from scattering to clear. This polymer is stable and resistant to water uptake. The transition temperature can be adjusted to a value comprised between 30° C. and 70° C. for instance by selecting other mesogens (i.e. the fundamental unit of a liquid crystalline material that induces structural order) known in the art. This can be achieved for instance by varying the end groups or spacer groups in the siloxane-polystyrene block-copolymer system, containing cyanobiphenyls side groups. Liquid crystalline siloxane rings (FIG. 6) usually exhibit a sharper temperature range for the liquid-to-crystal liquid transition than the corresponding linear polysiloxanes due to their narrower molecular weight distribution. In the example of FIG. 6, transition occurs within a temperature interval of about 1° C.

The general formula of a series of liquid crystalline siloxane rings is depicted below:

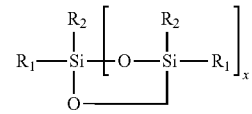

wherein x is 3 or 4, and wherein $R_1$ is a lower alkyl group (such as —$CH_3$, —$C_2H_5$), a $C_{3-10}$ cycloalkyl group (such as, but not limited to, cyclohexyl) or phenyl. Non limitative examples of mesogen $R_2$ groups include, but are not limited to, the following:

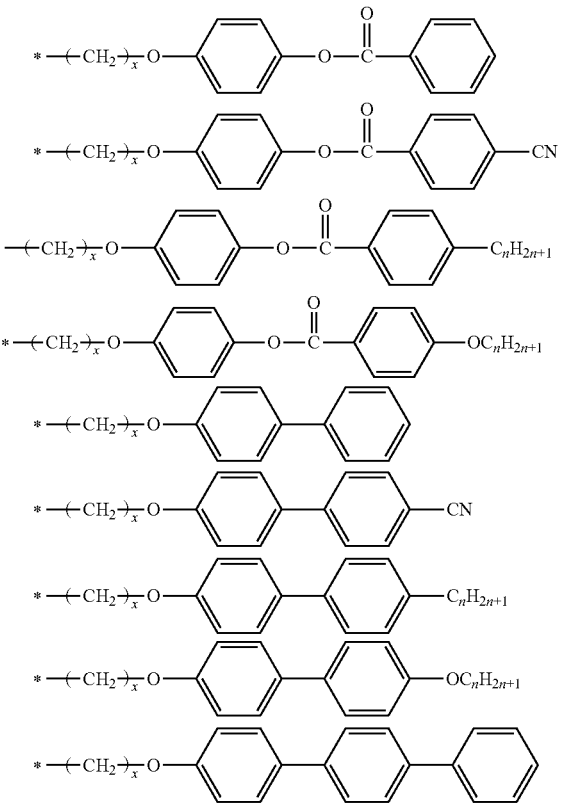

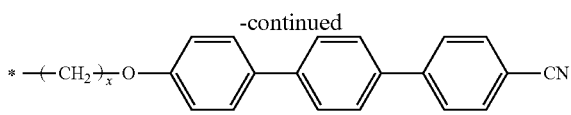

wherein x is preferably from 2 to 12 and wherein n is preferably from 1 to 6.

According to an embodiment of the present invention, low molecular weight, polymeric, oligomeric or cyclic liquid crystals may be blended with one or more hydrogel-forming monomers or dissolved therein. The solution or blend is subsequently polymerized. This permits to disperse efficiently the liquid crystals into the polymer hydrogel and to avoid to a large extent contact between the liquid crystalline material and the skin. The system forms then a so-called polymer-dispersed liquid crystal which is distributed in the form of droplets or channels within a polymer matrix.

An alternative way to prevent contact of the liquid crystalline material with the body (e.g. skin) is encapsulation of liquid crystal droplets within a polymer shell. Liquid crystal filled polymer capsules can for example be obtained by emulsifying a mixture of a polymer, a liquid-crystalline material and an organic solvent totally or partially miscible with water (such as, but not limited to, dichloroethane) in water. A stabilizer such as polyvinyl(alcohol) can also be added. The organic solvent dissolves in the water phase and subsequently evaporates. As a result, the polymer and the liquid crystal in the emulsion droplets are no longer miscible and a polymer shell is formed at the interface with the water phase. In order to improve the homogeneity of the size distribution of the LC-filled polymer capsules in the mixture of polymer, LC and solvent can be injected drop-wise in the water by making use of, for instance, an ink-jet nozzle. In the case of the use of ink-jet nozzles, capsule diameters may be in the 2-20 micron range. After removal of water, the capsules can be dispersed in a hydrogel forming monomer system and the resulting blend can be cured e.g. by photo-polymerization. Another advantage of this method is the possibility to use low molecular weight liquid crystals without a risk of water uptake or diffusion problems.

In an exemplary embodiment, LC-filled polymer capsules were prepared having a diameter of about 7 μm. When the capsules are observed between two crossed polarizers or between parallel polarizers, at a certain temperature above room temperature (e.g. at 35° C.), the contrast disappears and the capsules becomes invisible/transparent. In another embodiment of the present invention, an enhancement of the transition visibility from a scattering state to an isotropic state is achieved by adding a suitable amount of a dye to the liquid crystal system. The dye concentration is selected by the skilled person to make the dye hardly visible in the isotropic phase but clearly visible in the scattering phase. This is possible because the light pathway is longer in the latter.

As an optional feature of any of the embodiments above, a coloring agent, preferably a fluorescent dye or fluorescent beads may be comprised within the temperature indicating element. This feature is advantageous because it renders the temperature transition more visible. This can for instance be achieved by forming a layer comprising a dye, or a polymer containing a dye, under the hydrogel layer, or by enclosing a dye or a polymer containing a dye within the hydrogel. If a fluorescent dye is used, an artificial light source may be provided, so that transition detection can be performed by the same detection means used to detect the change in optical property (e.g. a microscope, a photodetector, a photodetector array, a camera such as CCD or CMOS camera, optical fibers, etc.).

In one embodiment of the present invention, frustrated total internal reflection (FTIR) may be used to detect the change in optical property. In this embodiment, the temperature indicating element of the present invention comprises a temperature detection surface on which one or more temperature indicating agents operating by changing an optical property at a predetermined temperature are present. For instance, in an embodiment of the present invention, the temperature detection surface may have, deposited at its surface as one or more layers and/or spots, at least one agent which indicates temperature through a change in an optical property. The change in an optical property indicating a change in temperature advantageously may result in an optical response, e.g. by frustrating the total internal reflection of an incident electromagnetic beam. This is for instance the case when the temperature indicating agent operates by becoming scattering. In another embodiment of the present invention, when the temperature indicating element comprises a temperature detection surface, the change in an optical property indicating a change in temperature advantageously operates by affecting the critical angle of reflection of an incident electromagnetic beam. This is for instance the case when the temperature indicating agent operates by changing its refractive index. The means for emitting incident electromagnetic radiation may for instance be an electromagnetic radiation source such as but not limited to a laser or a light emitting diode (LED), optionally provided with some optics for shaping and directing the incident electromagnetic radiation beam. Moreover, it should be noted that the occurrence of total internal reflection requires that the refractive index n1 of the temperature detection surface is larger than the refractive index n2 of the material adjacent to the detection surface (e.g. the temperature indicating agent). This is for example the case when the carrier is made from glass (n1=1.5) and the adjacent material is a hydrogel comprising mainly water (n2=1.3). The carrier may for example be produced from glass or some optically transparent plastic. When frustrated total internal reflection (FTIR) is used to detect the change of optical property, means for determining the intensity of electromagnetic radiation reflected from the temperature detection surface can be provided as a part of the transducer device or separated therefrom. In yet another embodiment of the present invention, the transducer device comprises both, means for emitting incident electromagnetic radiation, and means for determining the intensity of electromagnetic radiation reflected from the temperature detection surface. In another embodiment of the present invention, the temperature detecting agent operates by changing its refractive index and the interface between said temperature indicating agent and said temperature detection surface has been made rough or has been corrugated. In this embodiment, the temperature transition may be detected by measuring a change in reflection pattern.

In another embodiment of the present invention, the temperature indicating agent (e.g. the liquid crystalline/hydrogel material itself) is intrinsically colored or fluorescent.

In another embodiment of the present invention, different liquid crystalline materials having different liquid crystalline-to-liquid transition temperatures are deposited at different locations of the hydrogel. In this embodiment, a more precise determination of the exact temperature can be assessed rather than merely concluding on the fact that the tissue (skin or mucosa) is either above or under a certain critical temperature.

In another embodiment of the present invention, two temperature indicating elements (e.g. LC materials or temperature sensitive hydrogels) with a slightly different temperature transition are printed next to each other onto the hydrogel layer or are included in any other way into the temperature indicating element (e.g. each temperature indicating element can be a hydrogel layer having a LCST different from its neighboring layers, the ensemble of those layers forming the temperature indicating element). In another embodiment of the present invention, a plurality of temperature indicating elements (e.g. LC materials or temperature sensitive hydrogels) each with a different temperature transition are printed next to each other onto the hydrogel layer or are included in any other way into the temperature indicating element. In certain embodiments of the present invention, patterning means like photolithographic means (to pattern different spots or strips or any other shapes) may also be included. For instance, one temperature indicating agent (e.g. a LC material) may have a transition slightly below the desired temperature and the other one may have a transition temperature slightly above this temperature. By analyzing the two elements with the detection means (e.g., a microscope, a photodetector, a CMOS or CCD camera, etc.), the temperature can be accurately controlled between the two extremes given by the transition temperatures of these two different LC materials. Also the temperature indicating agents can be distributed over the surface of the hydrogel layer in order to obtain information about the temperature distribution over this surface.

In another embodiment of the present invention, cholesteric liquid crystals may be used as temperature indicating agents. Cholesteric liquid crystals are rod-like liquid crystals having a liquid-crystalline phase in which molecules are closely aligned within a distinct series of layers, with the axes of the molecules lying parallel to the plane of the layers and with the orientation of molecules in adjacent layers being slightly rotated. Because the LC molecules of a particular layer are always slightly rotated in one direction (e.g. clockwise) when compared to the LC molecules presents in the layer just below them, each inter-layers column of LC molecules describes a helix in the direction perpendicular to the molecules. Because of the molecular anisotropy, the uniaxial optical indicatrix also describes a helix into the same direction and reflection of light will occur when Bragg's conditions are met. The reflection wavelength λ relates to the helicoidal pitch p as follow:

$$\lambda = \bar{n} \cdot p,$$

wherein $\bar{n}$ is the average refractive index. The pitch p is temperature dependent and consequently, so is the reflection wavelength. The pitch becomes especially temperature sensitive when the cholesteric LC molecules are selected to exhibit a smectic phase at temperatures lower than the temperature wished to be monitored. The smectic phase unwinds the helix when the transition is approached and the color changes very steeply with temperature. Simple temperature indicating elements can be made by microencapsulating the liquid crystal and disperse the capsules into a hydrogel-forming monomer system. The resulting blend can then be cured e.g. by photo-polymerization.

The temperature information can be read from the reflection color. In this case spectral analysis will give the best results. A suitable analyzing means may for instance be a CCD camera provided with a color filter array.

The temperature indicating element may also serve as a physical proof or documentation of the lack of superficial damage to the patient's skin.

In the following non-limitative examples, a few temperature indicating agents suitable for use in certain embodiments of the present invention are described.

EXAMPLE 1

65 parts by weight of a polymer (commercially available from Merck under the name LCP93; formula below, degree of polymerization m+n=40; smectic to isotropic transition according to Merck at 97° C.)

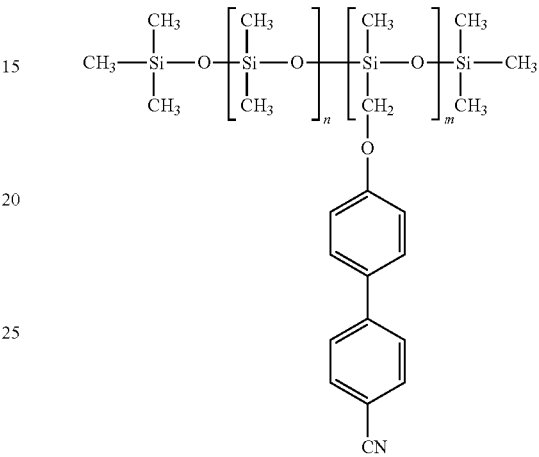

were mixed with 35 parts by weight of ethoxylated bisphenol-A diacrylate (trade name Sartomer 349, commercially available from Sartomer, Inc, U.S.A. Both materials have a similar refractive index of around 1.55 avoiding light scattering when the liquid crystal polymer LCP093 is heated above its liquid crystalline transition temperature. For curing the sample is blended with 2 parts by weight photoinitiator (trade name Irgacure 651 commercially available from Ciba Specialty Chemicals, Switzerland). The mixture forms a paste that can be printed by means of a PDMS mould onto a substrate. Curing proceeds by illumination with a UV source PL10 lamp (Philips—365 nm light at an intensity of 0.6 mW·cm$^{-2}$). The sample changes its appearance from highly scattering to clear transparent when heated above 74° C. The transition proceeded between 73 and 75° C.

EXAMPLE 2

The liquid crystal molecule of FIG. 6 was mixed with the bis-acrylate of ethoxylated bisphenol-A. UV light was used to photopolymerize the mixture in the presence of a photoinitiator (2 wt % Irgacure 651 commercially available from Ciba Specialty Chemicals, Switzerland). The transition temperature from scattering to clear was then observed between 60 and 61° C. with a charge-coupled device (CCD) camera.

EXAMPLE 3

A mixture of a biocompatible polymer (poly-(lactic-co-glycolic)acid, PLGA), a liquid crystal (n-pentylcyanobiphenyl) and dichloroethane (DCE) as a solvent was injected in water (PLGA:LC:DCE ratios being 0.05:0.20:99.75, and 0.3% by weight polyvinyl alcohol being added to H$_2$O as a stabilizer to prevent the emulsion droplets from coalescing) through ink-jet nozzles and LC-filled polymer capsules where obtained. After removal of water, the capsules were dispersed in a monomer system (ethoxylated bisphenol-A+2 wt % Irgacure 651 from Ciba Specialty Chemicals) and the resulting blend was cured by photo-polymerization of the monomer system. The transition temperature from scattering to clear was then observed at 35° C. and occurred within a temperature interval of not more than 1° C.

EXAMPLE 4

In this example, a temperature indicating agent having a transition temperature centered on 37° C. is provided.

First, a blend is made containing the following components:
50.3 wt-% of a liquid crystal mixture,
48.0 wt-% of a blend of reactive monomers, and
1.75 wt-% of a photoinitiator.

The liquid crystal mixture used contains two materials:
25 parts by weight:

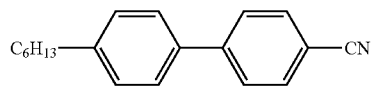

75 parts by weight:

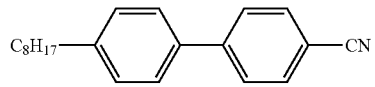

The blend of reactive monomers contains the following two materials:
75 parts by weight:

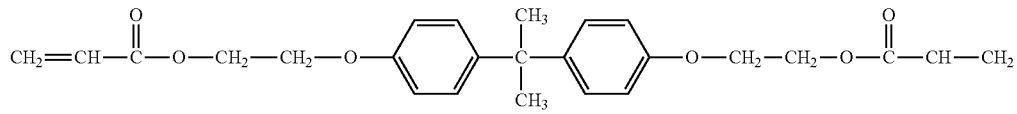

and 25 parts by weight:

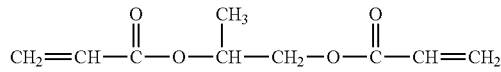

The photoinitiator was Irgacure 651 from Ciba Specialty Chemicals.

The mixture was photopolymerized by UV light. After polymerization the liquid crystal phase separates from the polymer matrix and is light-scattering. When heated above 37° C., the printed dots become highly transparent because the liquid crystal mixture goes through its phase transition to isotropic.

EXAMPLE 5

The same procedure as in example 5 was followed except that the blend further incorporated a dye and therefore contained the following components:
50.0 wt-% of the same liquid crystal mixture
48.0 wt-% of the same blend of reactive monomers
1.75 wt-% of the same photoinitiator, and
0.25 wt-% of a dye The dye was a sulphoindocyanine fluorescent dye (structure shown below) known as Cyanine-5.18 which emits at 667 nm:

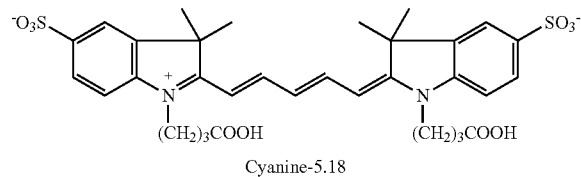

Cyanine-5.18

When excited with light of 650 nm or below the dots fluoresce. When heated above 37° C., the fluorescent intensity suddenly drops by an order of magnitude because the printed dots become highly transparent and non-scattering.

EXAMPLE 6

In this example, a temperature indicating agent was made with a transition temperature of about 61° C. The transition operates within a temperature interval of not more than 1° C.

In this case the same basic composition has been chosen as given in example 4. However the liquid crystal has been replaced with E7, a commercial mixture containing the following materials:

51 parts by weight n-pentylcyanobiphenyl, parts by weight n-heptylcyanobiphenyl, 16 parts by weight n-octyloxycyanobiphenyl, and 8 parts by weight n-pentylcyanoterphenyl.

The mixture was then photopolymerized by means of UV light. After polymerization the liquid crystal phase separates from the polymer matrix and is light-scattering. When heated above 61° C., the printed dots become highly transparent because the liquid crystal mixture goes through its phase transition to isotropic.

EXAMPLE 7

The same procedure as in example 7 was followed except that the blend further incorporates a dye and therefore contains the following components:

50.0 wt-% of the same liquid crystal mixture as in example 6, 48.0 wt-% of the same blend of reactive monomers as in example 6, 1.75 wt-% of the same photoinitiator as in example 6, and 0.25 wt-% of a dye.

The dye is a red-fluorescent dye ($\lambda_{ex}$630 nm; $\lambda_{em}$670 nm) (described in J. R. Fries et al. (2001) Chimica Oggi, 19, 18) having the following formula:

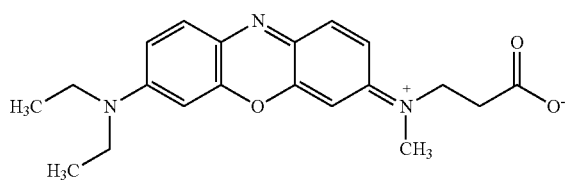

When excited with light of 630 nm, the dye fluoresce. When heated above 61° C., the fluorescent intensity suddenly drops visibly because the printed dots become highly transparent and non-scattering.

EXAMPLE 8

A solution of 49 weight % of N-isopropylacrylamide (NIPA) (monomer) mixed with diethylene glycol diacrylate (crosslinking agent), 1 weight % Irgacure 2959 and 50 weight % methanol was made. The mole ratio N-isopropylacrylamide:diethylene glycol diacrylate was 180:1. To this solution fluorescent beads (Crimson™ microspheres having a diameter of 0.02 μm) were added. The solution was polymerized under UV radiation. After rinsing the hydrogel in water (for removing methanol), the transition temperature (LCST) was observed around 32° C. via a change in fluorescence intensity recorded with a charge-coupled device (CCD) camera.

EXAMPLE 9

Hydrogels were prepared by following the same procedure as in example 8 except that the nature of the monomer, additional comonomer and cross-linker was according to table 1 below:

| Monomer | Comonomer | Crosslinker | LCST (° C.) |
|---|---|---|---|
| NIPA | / | A-HPC (hydroxypropyl cellulose) | 32.2 |
| VCL | GMA (Glycidyl methacrylate) | MBA | 32.8 |
| NIPA | | ACR-CELL | 34.1 |
| NIPA | VCL | MBA | 36.7 |
| NIPA | VP (N-vinyl pyrolidone) | ACR-CELL | 40 |
| DMAA (dimethylacrylamide) | GMA | MBA | 47.1 |
| NIPA | VP | MBA | 48.6 |
| NIPA | DMAPMA (dimethylaminopropyl methacrylamide) | MBA | 54.6 |
| NIPA | HMAA (N-(hydroxymethyl)acrylamide) | ACR-CELL | 55.2 |
| VCL | DMAPMA | MBA | 58.0 |

The LCST temperatures were measured by recording the change in turbidity.

EXAMPLE 10

Solutions comprising 250 mg N-isopropylacrylamide (NIPA), 5 mg diethylene glycol diacrylate (DEGDA), 15 mg Irgacure 2959 (photoinitiator), polyethylene glycol diacrylate (PEGA) (comonomer), and 80% water were prepared. The mole ratio of PEGA was varied form 0 to 9% with respect to NIPA. The solutions have been photo-polymerized by UV irradiation. By increasing the ratio of PEGA, the LCST could be varied between 36 and 47° C.

EXAMPLE 11

In this example, poly (N-isopropyl-acrylamide) in an aqueous solution is used. Poly(N-isopropylacrylamide) CAS Number 25189-55-3, molecular formula $(C_6H_{11}NO)_n$ was obtained from Aldrich. The average molecular weight (Mn) was between 20,000 and 25,000.

Different dilutions of this polymer were performed in MilliQ water in a ratio ranging from 1:10 (w/w) to 1:100 (w/w). The optical contrast at the phase transition was good through all this ratio range at about 32° C. Those preparations showed a relatively low viscosity and were therefore used inside a reservoir (e.g. a plastic bag). Such a reservoir filled with a temperature indicating agent could be used as a temperature indicating element despite the low viscosity of the Poly (N-isopropyl-acrylamide) solution used.

This example illustrates embodiments of the present invention wherein the temperature indicating agent is a low viscosity polymer or hydrogel.

As an advantageous feature, the viscosity of such a low viscosity polymer or hydrogel can be adapted by adding a gelling agent such as e.g. gelatine in order to form a hydrogel with the poly(N-isopropylacrylamide) suspended into the gelling agent matrix.

In a second aspect, the present invention relates to a device comprising means for emitting ultrasound energy onto a mammalian body having a temperature indicating element placed onto it, optionally means for detecting a change in optical property of the temperature indicating element, and means for adapting the power output of the means for emitting ultrasound energy in function of the detected change in optical property of the temperature indicating agent. In some embodiments of the present invention, the means for detecting a change in optical property are part of the device, in some other embodiments, these means are not part of the device. The device according to this aspect of the invention allow good control of the temperature at the surface of a mammalian body. The means for emitting ultrasound energy may be any such means but are preferably means for emitting high intensity focused ultrasound. In an embodiment, the means for emitting ultrasound energy comprise a transducer (i.e. means for converting electrical energy into ultrasound energy), preferably a large aperture transducer. Large aperture transducers are advantageous because they allow the distribution of acoustic energy to be placed over a large surface area in the proximal structure (skin, fat, muscle, etc.). The transducer can be composed of a multiplicity of transducer elements which can be switched off or have their emission intensity tuned either individually or in a grouped manner (e.g. an entire row of elements, or the whole set of elements). This embodiment is advantageous because it allows for instance to turn off certain transducer elements to avoid discomfort or burns at specific skin locations but allow the treatment to continue at other body locations. This is for instance useful when the temperature is very locally increased because of the presence of an air bubble or other localized acoustic absorption onto the relevant tissue (e.g. skin). The transducer is meant to be used together with a power source but of course, such power source does not have to be part of the device. The means for emitting ultrasound energy therefore optionally comprise such power source. The power source can for instance be a generator generating a controlling electrical signal which is applied, e.g. through an attachment cable, to the transducer. In an embodiment, the means for detecting a change in optical property of the temperature indicating element comprise a light detector. Examples of light detectors are photodetectors, CMOS or CCD cameras, photodiode, a photo resistor, a photocell, or a photo multiplier tube among others. For the detection of light within cavities, e.g. if the temperature indicating element is applied on an internal mucosa, the light detector can advantageously be a fiber optic catheter. For a change in optical property to be detectable, a light source is required but, off course, this light source does not have to be necessarily part of the device according to the present invention. In embodiments of the present invention, the light source is not part of the device and in other embodiments, the light source forms part of the device. The light source may be of any origin, for instance it can be a natural light source such as the sun or it may be an artificial light source. Examples of suitable light sources comprise but are not limited to a laser or a light emitting diode (LED), optionally provided with some optics for shaping and/or directing the incident electromagnetic radiation beam. For the emission of light within cavities, e.g. if the temperature indicating element is applied on an internal mucosa, the light source can advantageously be a fiber optic catheter. As already mentioned, the light source(s) and/or the detector(s) may either form part of the transducer device or may be separated from the device. Often the direct line of sight between the transducer and the relevant tissue (e.g. skin) should be prevented. For this reason, it is advantageous in some embodiments of the present invention to use a light detector and lighting system slightly next to the transducer or to use optical means such as mirrors or optical wave guiding elements (optical fibers etc.) to redirect the emitted or received light in an appropriated manner. In certain embodiments of the present invention, use may be made of waveguides, such as e.g. thin transparent wave-guiding films, to guide the light through the optical wave-guiding structure either from the emitter toward the temperature indicating element or from the temperature indicating element toward the light detector. When a wave guide is used, it may be positioned onto or close to the tissue surface. In another embodiment, the wave-guide can be an additional layer attached to the hydrogel layer or can be the hydrogel layer itself. For instance the wave-guide can be constructed by superposing layers (e.g. polymeric or hydrogel layers) having different refractive index, e.g. a three layer structure composed of an internal layer having a high refractive index and a top layer and a bottom layer each having a lower refractive index. Of course, an optical fiber is another example of a wave-guide that can readily be used for performing the invention.

In a preferred embodiment of the present invention, the light detector can deliver a signal comprising temperature related information to a controller, which in turn can modulate the energy output of the means for emitting ultrasound energy in function of the signal. This modulation can be in the form of a starting of the means for emitting ultrasound energy, stopping those means or setting the power to an intermediate level. A feedback process may therefore be implemented in which the controller receives the signals corresponding to the temperature readings, and adjusts power output to the means for emitting ultrasound in order to avoid heat related damage at the level of the mammalian's skin. In a preferred embodiment, the controller switches off the means for emitting ultrasound energy when the detected temperature at the level of the temperature indicating agent is at or above a predefined temperature. In other embodiments of the invention, instead of switching of the means for emitting ultrasound energy, the controller may tune the intensity of the ultrasound output by e.g. reducing the energy of the ultrasounds used, varying the pulse frequency of the ultrasound waves, momentarily interrupting the ultrasound output, among others). Since the temperature element of the present invention permits to evaluate the temperature of a surface and therefore also the homogeneity thereof, the tuning of the ultrasound output may be operated by varying the ultrasound output precisely hitting the tissue at the place where overheating occurs. For instance, less energy can be applied at a hot spot where e.g. gas or a hair is at the skin-temperature indicating agent interface. Also, more energy can for instance be put in regions with a lower temperature. So a tuned ultrasound exposition (patterned power) can be obtained.

Useful such predefined temperatures are e.g. 30° C., 35° C., 40° C., 45° C., or 48° C., or any temperature between about 30° C. and bout 48° C. As an optional feature, means for recording the temperature-related information gained may be provided. This is advantageous because it can serve as proof that critical temperature has not been overpassed at the level of the patient's skin.

FIG. 7 is a schematic representation of a device according to a particular embodiment of the present invention. It comprises means for emitting ultrasound energy 3 and 11, wherein 3 is a transducer and 11 is a generator delivering an electrical signal to the transducer 3, which in turn will transform this electrical signal in an ultrasound signal. A temperature indicating element 1 is placed on the skin 2 of a mammalian body in the ultrasound path between the transducer 3 and the area to be exposed to the ultrasound waves. An external light source 8 is placed in such a way as to permit the lateral irradiation 9 of the temperature indicating element 1. The light detector 6 is placed in such a way as to enable the detection of the temperature indicating signal 7. Once signal 7 is received, the controller 10 uses the temperature related information contained in the signal to adapt the power output of the means for emitting ultrasound energy 3 and 11.

Figure 1:
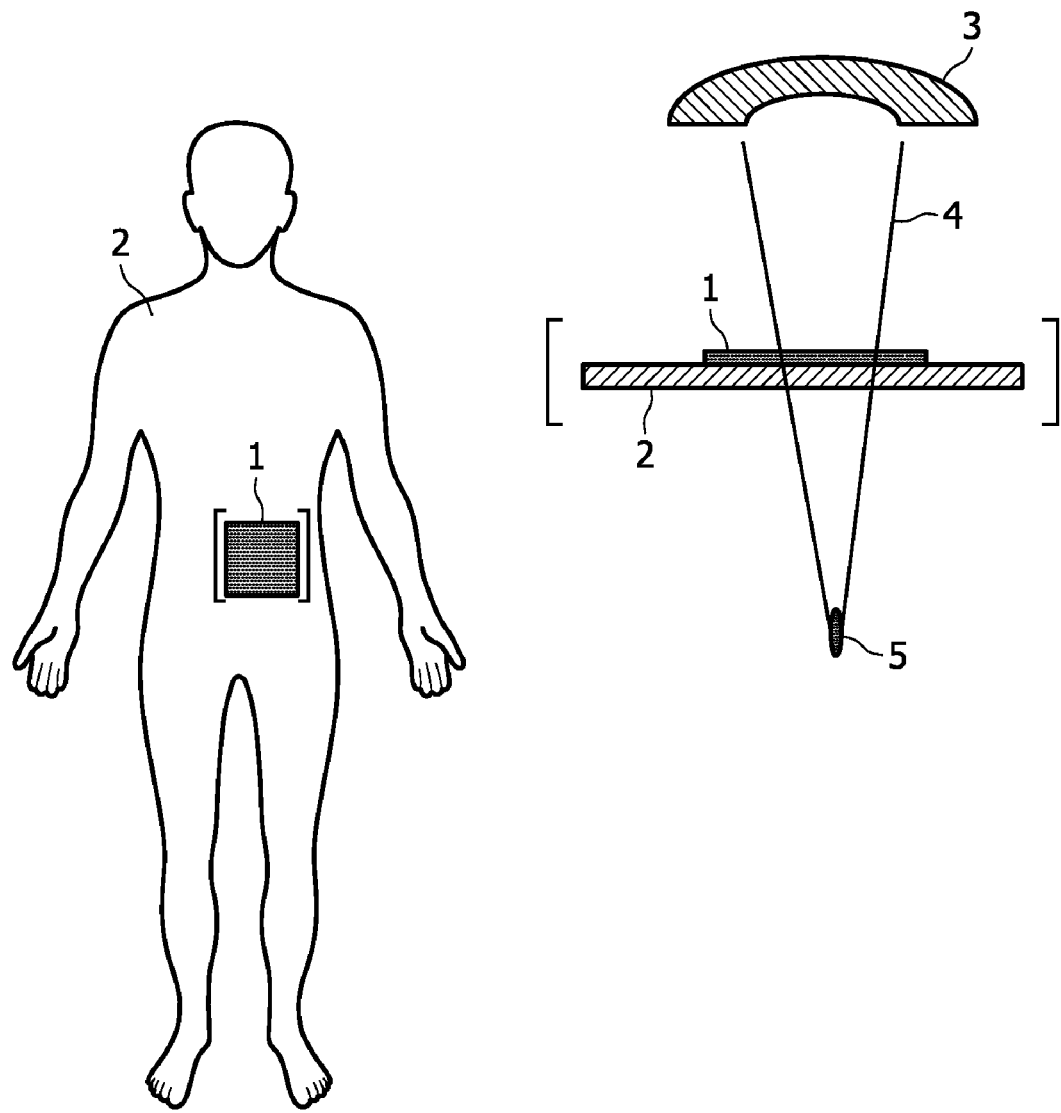
FIG. 1 is a schematic representation of a top-view (left) and a side-view (right) of a temperature indicating agent according to an embodiment of the present invention present on a human body during a focused ultrasound experiment.
Figure 2:
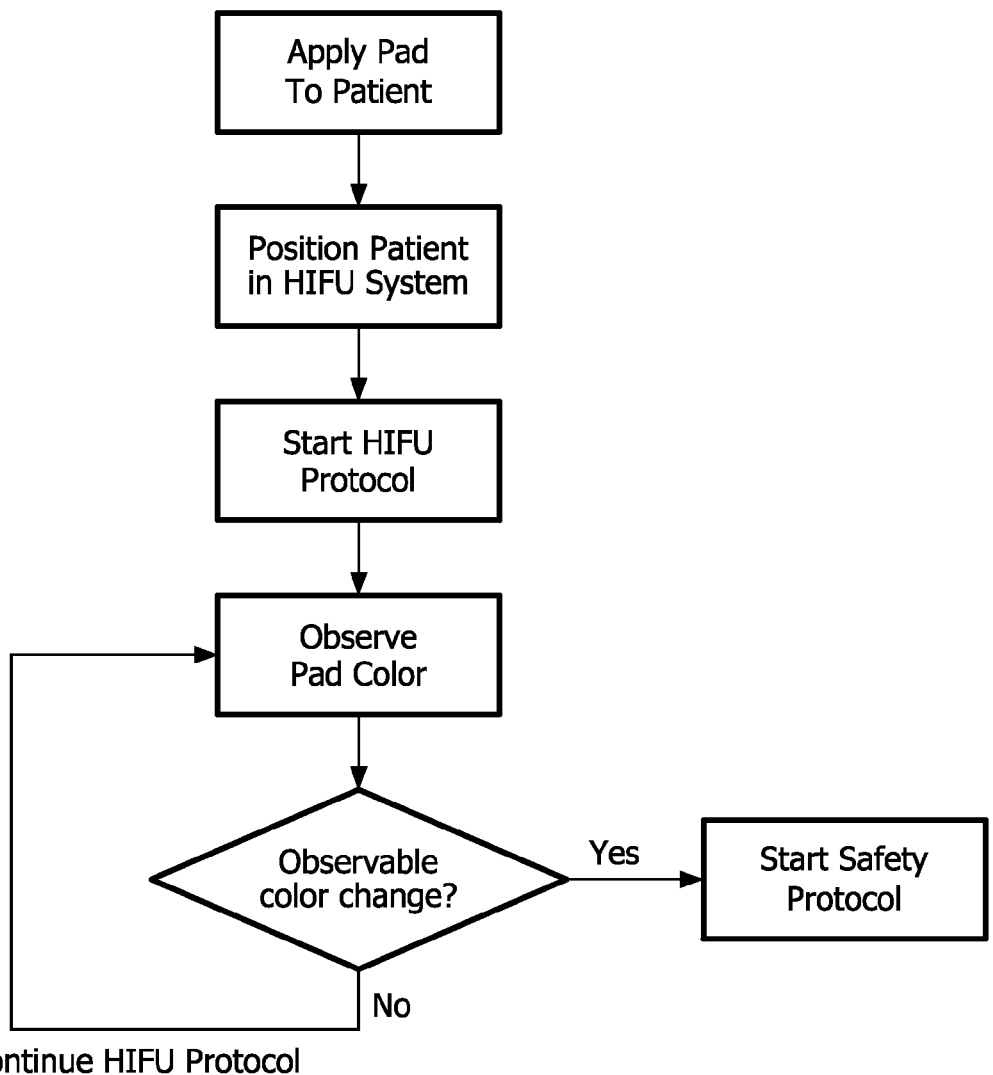
FIG. 2 is a flowchart showing a therapeutic method according to an embodiment of the present invention.
Figure 3:
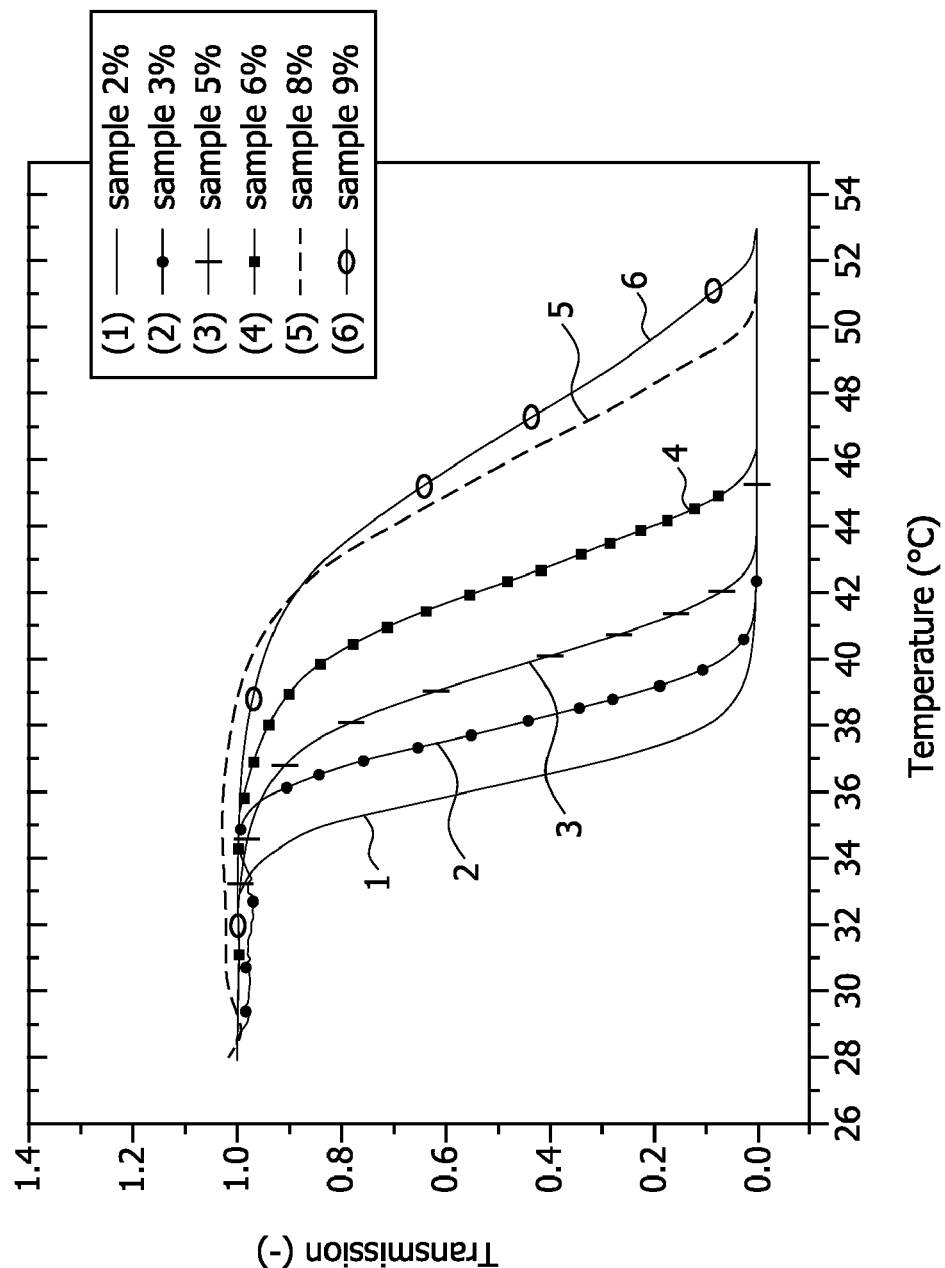
FIG. 3 is a graph of the light transmission versus temperature in 6 different hydrogels used in embodiments of the present invention.

In a another aspect, the present invention relates to a therapeutic or diagnostic method. In an embodiment, the therapeutic or diagnostic methods according to the present invention comprise the placing of a temperature indicating element, according to any of the embodiments of the first aspect, on a tissue (e.g. skin or mucosa) of a mammalian body. In embodiments of the present invention, the method further comprises the step of exposing the mammalian body to ultrasound energy. FIG. 2 illustrates a specific embodiment of the third aspect of the present invention. First a temperature indicating element, here a hydrogel pad, is applied on the skin of the patient. The patient is then positioned in a high intensity ultrasound system. Next, the high intensity ultrasound therapeutical protocol is started and the color/opacity of the hydrogel is observed/monitored. If a change in optical property is observed, a safety protocol is started. This includes for instance switching off the means for emitting ultrasounds. If no optical property change is observed, the high intensity ultrasound therapeutic protocol is maintained until the optical property change is observed. The present invention may for instance be used be used for treating lesions within the female breast. In such a case, the geometry will often not allow for an ultrasound transducer to be placed at sufficient distance from the breast to avoid the near field of the ultrasound field. As a consequence, the intensity experienced at the skin surface may be sufficient to cause negative effects of heating. In such a case, a temperature indicating element as proposed in the first aspect would be useful for monitoring the unwanted heat deposition. In addition, the positioning of a temperature indicating element on the distal side of the breast may be useful for checking on the amount of ultrasound that is absorbed through the breast.

In a another aspect, the present invention relates to a method to gain temperature related information about the tissue (e.g. skin or mucosa) of a mammalian body, said method comprising the step of placing a temperature indicating element according to any embodiments of the first aspect of the present invention on the tissue (e.g. skin or mucosa) of a mammalian body.

In an embodiment of the latter aspect of the present invention, the method may be preformed while the mammalian body is exposed to ultrasonic waves, and the method then further comprises the detection of a change in the optical properties of said temperature indicating agent.

In a another aspect, the present invention relates to a method for controlling the power output of a ultrasound transducer, said method comprising the steps of placing a temperature indicating element according to any embodiments of the first aspect of the present invention on the tissue (e.g. skin or mucosa) of a mammalian body, detecting a change in the optical properties of said temperature indicating element and feeding the information related to said change to a controller adapted to modulated said power output in function of said information.

In a another aspect, the present invention relates to the use of a temperature indicating element according to any embodiments of the first aspect of the present invention for monitoring the temperature of the tissue (e.g. skin or mucosa) of a mammalian body.

Other arrangements for accomplishing the objectives of the various aspects embodying the invention will be obvious for those skilled in the art. For instance, the temperature indicating element can be used to gain temperature-related information from the surface of the transducer itself since its temperature is preferably also monitored. In the prior art, this transducer temperature monitoring is made by using thermocouples. The use of thermocouples only confers point reading of the temperature while the use of the temperature indicating elements according to certain embodiments of the present invention permits to gain information about the distribution of temperature onto the surface of the transducer.

It is to be understood that although preferred embodiments, specific constructions and configurations, as well as materials, have been discussed herein for devices according to the present invention, various changes or modifications in form and detail may be made without departing from the scope and spirit of this invention.

The invention claimed is:

1. A system for controlling an ultrasound energy emitter, the system comprising:
   a temperature indicating element configured to apply topically on skin of a mammalian body in a path between the ultrasound energy emitter and an area on the body to be exposed to the ultrasound waves, the element comprising a layer with a thickness ranging from 100 µm to 5 mm having one or more temperature indicating agents operating by changing an optical property, said layer comprising hydrogel transparent to ultrasound energy;
   a light source configured to irradiate the temperature indicating element, the irradiation generating a temperature indicating signal when laterally passing through the element;
   a light detector configured to detect the temperature indicating signal including temperature related information; and
   a controller connected to the light detector and the ultrasound energy emitter configured to adapt power output of the ultrasound energy emitter in accordance with the temperature related information.

2. The system according to claim 1, wherein the layer comprises an optical property that changes at a temperature ranging from 30° C. to 70° C.

3. The system according to claim 2, wherein said hydrogel comprises a polymer or copolymer having N-substituted acrylamide monomeric moeities.

4. The system according to claim 1, wherein said hydrogel comprises an acoustic impedance above or equal to 1.4 Mrayl and/or below or equal to 1.6 Mrayl.

5. The system according to claim 1, wherein said hydrogel comprises a density equal to or above 0.9 and/or equal to or below 1.1 g/cm$^3$ when saturated with water.

6. The system according to claim 1, wherein said hydrogel comprises a sound velocity equal to or above 1.3 mm/µs and/or equal to or below 1.75 mm/µs.

7. The system according to claim 1, wherein said temperature indicating element has a thermal conductivity k above or equal to 0.15 W/(m*K) and/or below or equal to 0.6 W/(m*K).

8. The system according to claim 1, wherein said temperature indicating element further comprising a laminated structure having two or more hydrogel layers.

9. The system according to claim 8, wherein at least two of said layers have a different acoustic impedance.

10. The system according to claim 8, wherein at least one of said layers is free of temperature indicating agent.

11. A device comprising:
    a temperature indicating element transparent to ultrasound energy having one or more temperature indicating agents operating by changing an optical property;
    an ultrasound emitter configured to emit ultrasound energy into a mammalian body through the temperature indicating element placed onto skin;
    a light source configured to irradiate the temperature indicating element, the irradiation generating a temperature indicating signal when laterally passing through the temperature indicating element;
    a detector configured to detect the temperature indicating signal including temperature related information; and
    a controller configured to adapt the power output of said ultrasound emitter in accordance with the temperature related information.

12. The device according to claim 11, wherein said controller switches off the emitter at least partially when the detected temperature is above 30° C.

13. The device according to claim 11, wherein said emitter emitting high intensity focused ultrasound energy.

14. A method to use temperature related information about a tissue of a mammalian body exposed to ultrasound energy to prevent burns, said method comprising acts of:
    placing a temperature indicating element having a layer transparent to ultrasound energy with a thickness ranging from 100 μm to 5 mm comprising one or more temperature indicating agents operating by changing an optical property onto said tissue of said mammalian body in a path of the ultrasound energy and an area on the body to be exposed to the ultrasound waves;
    irradiating the temperature indicating element, when light laterally passing through the element the irradiation generating a temperature indicating signal including temperature related information;
    adapting power output of the ultrasound energy in accordance with the temperature related information.

15. The method of claim 14, further comprising an act of detecting the temperature indicating signal is generated by a change in an optical property of said temperature indicating element.

16. A method for controlling power output of an ultrasound transducer, said method comprising acts of:
    placing a temperature indicating element having a layer transparent to ultrasound energy onto a tissue of a mammalian body in a path of the power output on an area on the body to be exposed to ultrasound waves;
    exposing said mammalian body to the ultrasound waves of the ultrasound transducer that pass through said temperature indicating element;
    irradiating the temperature indicating element, when light laterally passing through the element the irradiation generating a change in optical property of said temperature indicating element;
    detecting the change in optical property of said temperature indicating element, and
    transferring information related to said change in optical property to a controller for modulating said power output as a function of said change in optical property.

17. The method of claim 16, wherein the temperature indicating element comprises a layer with a thickness ranging from 100 μm to 5 mm of a hydrogel as a temperature indicating agent.

18. The method according to claim 17, wherein said layer comprising hydrogel is transparent to ultrasound energy.

19. The method of claim 16, wherein the temperature indicating element comprises hydrogel having a temperature indicating agent or one or more temperature indicating agents operating by changing an optical property for monitoring the temperature of a tissue of a mammalian body exposed to ultrasound energy.

20. The method of claim 19, wherein said hydrogel comprises a polymer or copolymer having N-substituted acrylamide monomeric moeities.

* * * * *